Oct. 5, 1971 J. B. WILLIAMS Plant Pat. 3,065
ROSE PLANTS
Filed Nov. 5, 1969
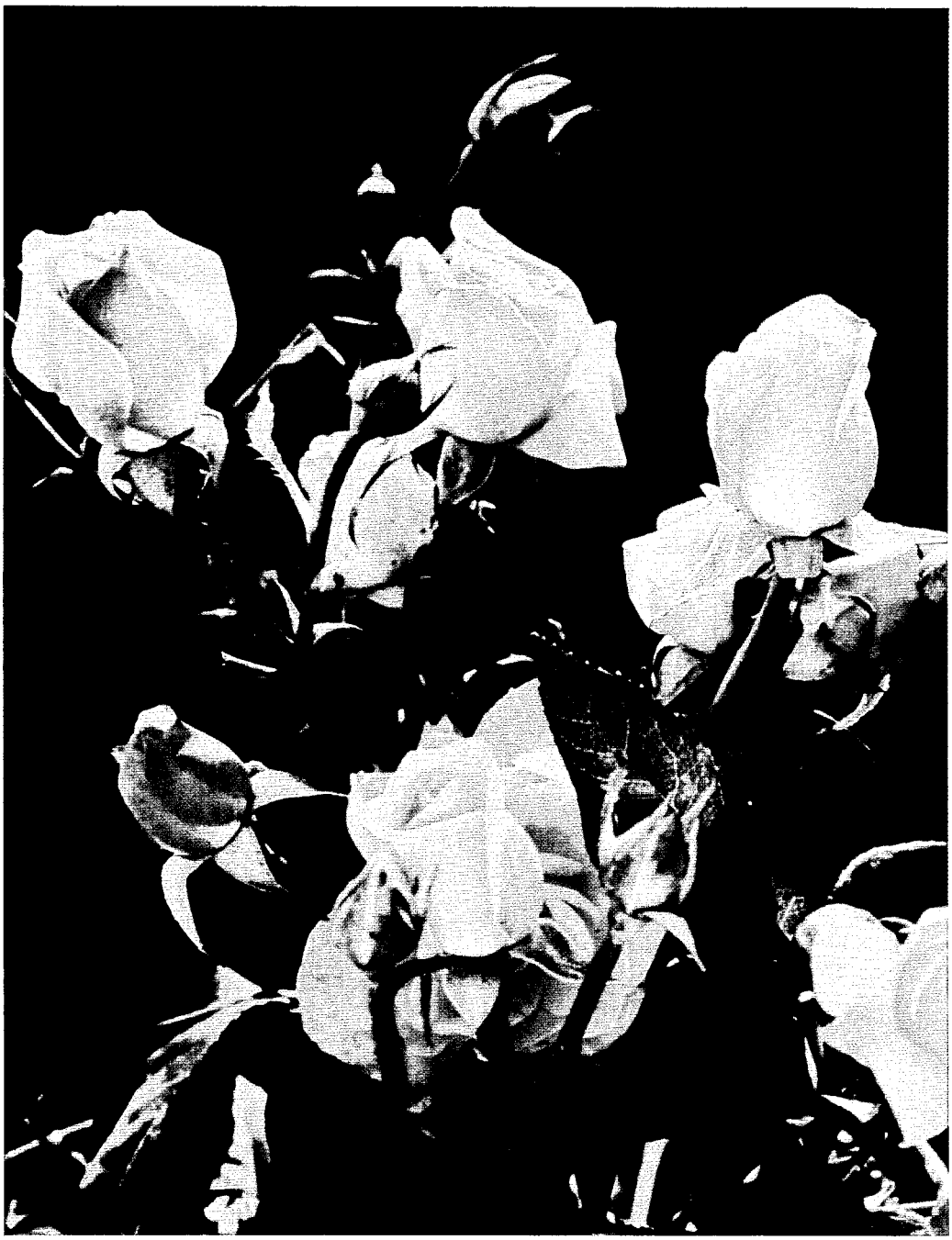
INVENTOR.
J. Benjamin Williams

United States Patent Office

Plant Pat. 3,065
Patented Oct. 5, 1971

3,065
ROSE PLANTS

J. Benjamin Williams, 2800 Elnora St., Silver Spring, Md. 20902

Filed Nov. 5, 1969, Ser. No. 874,422
Int. Cl. A01h *5/00*
U.S. Cl. Plt.—22 1 Claim

The present invention relates to a new and distinct variety of rose-plant of the floribunda class produced by crossing Queen Elizabeth (Plant Patent No. 1,259) with Sumatra (Plant Patent No. 1,572).

The primary objectives of this breeding were to produce a new rose variety combining the vigorous, heavy growth, the excellent disease resistant foliage and the outstanding blooming and keeping quality of Queen Elizabeth with the Orange Red color tones, bud form and freedom of bloom of Sumatra. I desired also to project into the seedlings of this breeding the recessive Orange Red color tones known to be present in the chromosomes of Sumatra, as a result of its parentage, as well as the desirable bloom characteristics known to be present in its parentage, along with the bush's low, compact, uniform growing habits.

That several of these objectives were achieved is evidenced by the following characteristics which, in combination, are unique and distinguish the variety from its parents and other varieties in commerce:

(1) The bright Red-Orange, well formed small hybrid tea type bud has a clear yellow base on the reverse and opens to a soft Coral Orange.

(2) The glossy Dark Reddish Green, abundant foliage.

(3) The strong, stocky habit of growth.

(4) The large well formed bloom sprays which continue to develop uniformly on a well balanced bush throughout the growing season from spring to frost giving a mass bloom effect.

Asexual reproduction of my new variety by budding as performed at West Grove, Pa., shows that the aforementioned characteristics are established and transmitted through succeeding propagations.

The accompanying drawing shows typical specimens of the vegetative growth and flowers of my new variety depicted in color as nearly true as it is reasonably possible to make the same in a color illustration of this character.

The following is a detailed description of my new variety, with color terminology in accordance with the Color Chart of the Royal Horticultural Society, London:

Type: Hardy, bush; outdoors; seedling; for cut flowers and for garden decoration.
Class: Floribunda.
Breeding:
*Seedling.*—Seed parent: Queen Elizabeth (Plant Patent No. 1,259). Pollen parent: Sumatra (Plant Patent No. 1,573).

*Flower*

(Observations made from specimens grown outdoors at West Grove, Pa., near mid-afternoon in the first part of July.)

Flowers borne: In clusters of from 3 to 5 on normal medium stems.
Quantity of bloom: Free outdoors.
Continuity: Continuous.
Fragrance: Medium centifolia.
Bud:
*Peduncle.*—Medium; medium heavy; erect; Green, 139C, overlaid with Red, 46C; smooth:
*Before calyx breaks.*—Size, small. Form, pointed ovoid with foliaceous appendages on the surface of the bud.

*As calyx breaks.*—Color, Red, 42A.
*As first petal opens.*—Size, small. Form: Pointed ovoid. Color: Outside—Orange Red, 39A, opening to Coral Pink, 50B. Inside—Coral Orange, 39C, finishing to Coral Pink, 50D.
*Opening.*—Opens up well.
Bloom:
*Size when fully open.*—Large, 3½ to 4 inches.
*Borne.*—Several together and in irregular clusters.
*Petalage.*—Double, from 35 to 40 petals.
*Form.*—Bud pointed at first, becoming high centered; open flower petals retaining firm recurled effect.
*Color when fully open.*—Coral, 52D, washing to 52B on edge of petal.
Petals:
*Appearance.*—Inside, satiny; outside, shiny.
*Texture.*—Leathery—is not affected by wet or hot weather.
*Form.*—Round, slightly notched.
*Arrangement.*—Imbricated (regularly arranged shingle-like).
*Inner.*—Few, small.
*Persistence.*—Drop off cleanly.
*Lasting Quality.*—On the plant, long; as a cut flower, long.

*Reproductive organs*

Stamens: Many; arranged regularly about pistils.
Filaments: Many; most with anthers; short length.
*Color.*—45D with base Yellow, 13B.
Anthers: All open at once: short.
*Color.*—Yellow, 10A.
Pollen: Moderate; Gold.
Pistils: Medium.
Styles: Uneven; short; thin; bunched.
Stigma: Pink.
Ovaries: All enclosed in receptacle.
Hips: None observed.
Seeds: None observed.
Sepals: Permanent; moderately short; straight spear shaped.

*Plant*

Foliage:
*Leaves.*—Compound of 5 to 7 leaflets; normal; medium; moderately heavy glossy.
*Leaflets.*—Shape—oval with apex acute, margin simply serrate.
*Color.*—Mature—upper surface: Green, 137A, distinctly overlaid with Red, 46C, extending to leaf, rib, vain, and serration. Under surface: Green, 139C, margin. Young Upper surface: Red-Purple, 59A, lightly overlaid with Red, 46C. Under surface: Red, 59C.
*Rachis (the supporting stem of the compound leaf).*—Medium. Upper side—Grooved. Under side—Smooth.
*Stipulates.*—Medium; moderately narrow; turning out at an angle of more than 45°.
*Disease.*—Resistance superior to the average variety growing under the same cultural conditions.
Growth:
*Habit.*—Bushy; much branched.
*Growth.*—Moderate free.
*Canes.*—Medium.
*Main stems.*—Dull, smooth. *Color*—old wood, Green, 139A. *Color*—new wood, Red, 59A. *Prickles*—few—Red, 59B.
*Branches.—Color.*—Green, 137A, overlaid with Red, 59A. *Prickles.*—none. *Hairs.*—none.

I claim:

1. A new and distinct variety of rose plant of the floribunda class, substantially as herein shown and described, characterized particularly as to novelty by the Orange Red coloration of the open blooms, changing to soft Coral overlay, the abundant Dark Green Redcast glossy foliage, the strong, stocky habit of growth and the large flower spray and well formed blooms which exhibit a wide range of color variation in Orange Red and Coral tones, varying with the age of bloom, temperature and soil.

No references cited.

ROBERT E. BAGWILL, Primary Examiner